United States Patent [19]

Smith

[11] 4,123,444

[45] Oct. 31, 1978

[54] 2-ALKOXY-TETRAHYDROFURANS VIA HYDROFORMYLATION OF ALLYLIC ALCOHOLS

[75] Inventor: William E. Smith, Schenectady, N.Y.

[73] Assignee: General Electric Company, Pittsfield, Mass.

[21] Appl. No.: 806,073

[22] Filed: Jun. 13, 1977

[51] Int. Cl.$^2$ .......................................... C07D 307/20
[52] U.S. Cl. .................. 260/347.8; 260/615 AA; 568/867; 568/865
[58] Field of Search ...................... 260/347.8, 615 AA

[56] References Cited

U.S. PATENT DOCUMENTS

| | | | |
|---|---|---|---|
| 3,239,566 | 3/1966 | Slaugh et al. | 260/604 |
| 3,917,661 | 11/1975 | Pruett et al. | 260/410.9 R |

FOREIGN PATENT DOCUMENTS

| | | |
|---|---|---|
| 103,203 | 3/1962 | Czechoslovakia. |
| 2,538,364 | 3/1976 | Fed. Rep. of Germany. |

OTHER PUBLICATIONS

Adkins et al., Journal of the American Chemical society, vol. 70 (1948) pp. 383–386 and vol. 71 (1949) pp. 3051–3055.
Lawesson et al., Acta. Chem. Scand., vol. 14 (1960) pp. 1854 & 1855.
Brown et al., Tetrahedron Letters, vol. 22 (1969) pp. 1725 & 1726.
Brown et al., Journal of the Chemical Society (A) 1970, pp. 2753–2764.

*Primary Examiner*—Richard L. Raymond
*Attorney, Agent, or Firm*—Morgan, Finnegan, Pine, Foley & Lee

[57] ABSTRACT

2-Alkoxytetrahydrofurans are prepared by hydroformylation of an allylic alcohol in the presence of an alkanol and a rhodium hydroformylation catalyst. The products are useful, inter alia, as intermediates in the preparation of butanediols and substituted derivatives thereof.

11 Claims, No Drawings

2-ALKOXY-TETRAHYDROFURANS VIA HYDROFORMYLATION OF ALLYLIC ALCOHOLS

The present invention relates to the preparation of 2-alkoxytetrahydrofurans and their derivatives. More particularly it relates to the hydroformylation of allylic alcohols in the presence of a rhodium catalyst and an alkanol solvent/co-reactant.

BACKGROUND OF THE INVENTION 2-alkoxytetrahydrofurans and their derivatives are useful intermediates in the production of 1,4-diols and other valuable chemicals. See the co-pending application of William Edward Smith, entitled "Butanediols Via Hydrolysis-Hydrogenation of 2-Alkoxytetrahydrofurans" filed on even date herewith under Ser. No. 806,074, now U.S. Pat. No. 4,091,041 assigned to the same assignee as the instant application, and incorporated by reference herein.

There have been several reports describing the synthesis of 2-alkoxytetrahydrofuran derivatives. By way of illustration, Lawesson and Berglund, Acta. Chem. Scand. 14, 1854-5 (1960), generated a number of the subject compounds by decomposing t-butyl perbenzoate in the presence of alkanol-tetrahydrofuran mixtures. Furthermore, Kratochvil and Hort Czech. 103, 203 (1962), produced 2-methoxytetrahydrofuran by the low temperature photochlorination of tetrahydrofuran in the presence of methanol and an HCl acceptor.

It has also long been known that allyl alcohol can serve as a substrate for the hydroformylation reaction, affording hydroxyaldehyde products. Adkins and Kresek, Journal of the American Chemical Society, 70, 383 (1948) and 71, 3051 (1949) reported the synthesis of 4-hydroxybutyraldehyde in 30% yield by the cobalt carbonyl-catalyzed hydroformylation of allyl alcohol. Brown and Wilkinson, Tetrahedron Letters 1969, (22), 1725-6 and Journal of the Chemical Society (A), 1970, 2753-64, reported the hydroformylation of allyl alcohol and a number of other olefins in the presence of hydridocarbonyltris-(triphenylphosphine) rhodium (I) as catalyst, which produced the corresponding aldehydes. Pruett and Smith in U.S. Pat. No. 3,917,661 claim a process for producing oxo aldehydes from olefins using a rhodium carbonyl catalyst system modified by triorgano phosphorus ligands of the group consisting of trialkylphosphites, tricycloalkylphosphites, triarylphosphites, and triarylphosphines.

In German Pat. No. 2,538,364, Schimizu describes a process by which allyl alcohol is converted to an aldehyde mixture by hydroformylation in the presence of a rhodium carbonyl catalyst modified by any of a number of triorgano phosphorus ligands, and the aldehydes are separated by aqueous extraction and converted to butanediol in a separate, conventional hydrogenation procedure.

U.S. Pat. No. 3,239,566 of Slaugh et al discloses the use of phosphine-rhodium carbonyl complex catalysts in oxo reactions producing aldehydes and/or alcohols at temperatures exemplified at 195° C.

As a result of investigating the hydroformylation of allyl alcohol under the influence of a triphenylarsine-modified rhodium carbonyl catalyst, a minor product not encountered in previous studies with other catalyst systems, has now been isolated and identified as 2-n-propoxytetrahydrofuran. It appears that this compound is formed in a secondary reaction involving hydroformylation and hydrogenation derivatives of allyl alcohol. This point was then verified and a synthetically useful process has now been discovered, and is the subject of this invention. In essence, the hydroformylation according to this invention is to be carried out in the presence of a co-reactant quantity of an alkanol by the following pathway:

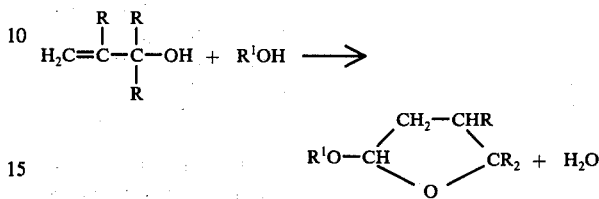

wherein R is hydrogen or alkyl and $R^1$ is alkyl or hydroxyalkyl.

In all cases, the corresponding 2-alkoxytetrahydrofuran is formed in good yield.

DESCRIPTION OF THE INVENTION

According to the present invention in its broadest aspects there is provided a process for preparing a 2-alkoxytetrahydrofuran or a 2-alkoxy-substituted tetrahydrofuran which comprises contacting an allylic alcohol, carbon monoxide, hydrogen and the corresponding alkanol with a rhodium hydroformylation catalyst.

Preferred features of the invention involve carrying out the process at an elevated pressure in the range of 100-5000 psi, and especially preferably from 300-1200 psi. Another preferred feature is to carry out the process at a temperature between about 25° C. and 200° C., especially preferably in the range of 100°-150° C. Still another preferred feature comprises using a catalyst comprising rhodium, rhodium carbonyl or rhodium supported on a carrier, or a catalyst which further includes a ligand selected from an arsine or a phosphine. In an especially preferred embodiment, the allylic alcohol comprises allyl alcohol, methallyl alcohol, or 2-methyl-3-buten-2-ol. Especially suitable alcohols comprises methanol, n-propanol, isopropanol or ethylene glycol.

By way of illustration, the allylic alcohol is selected from one of those of the forumla:

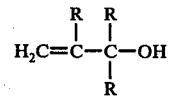

wherein R is hydrogen or alkyl from 1 to 8 carbon atoms and said alkanol is selected from among those of the formula:

$$R^1OH$$

wherein $R^1$ is alkyl of from 1 to 8 carbon atoms or hydroxyalkyl of from 2 to 8 carbon atoms.

The disclosed process can be operated in a manner typical of rhodium carbonyl-catalyzed hydroformylation processes. The catalyst may be generated in situ from elemental rhodium, rhodium oxide or rhodium trichloride (optionally introduced on an inert support such as carbon) or from such rhodium carbonyl compounds as hexarhodium hexadecarbonyl $[Rh_6(CO)_{16}]$ on contact with a suitable known ligand, carbon monoxide and hydrogen, or may be added in the form of a hydridocarbonyl rhodium species such as hydridocarbonyltris(triphosphine) rhodium (I). In addition, methods known in the art for generating arsine- and phosphine-modified rhodium carbonyl hydroformylation catalysts may also be used to make catalysts of the present process.

Suitable modifying ligands for metal carbonyls used as catalysts in the present hydroformylation processes, may include triphenylphosphine, triphenylphosphite, triphenylarsine, triphenylantimony, trimethylphosphite, tri-n-propylphosphite, tri(4-hydroxybutyl) phosphite, diphenyl sulfide, tri-o-tolylphosphine, triphenylphosphine oxide and the like.

The allylic alcohols used as starting materials for the present invention include compounds characterized by the basic allylic alcohol structural arrangement:

$$C=C-C-OH$$

A preferred family will be of the formula $$\begin{array}{cc} & R \quad R \\ & | \quad | \\ H_2C=C-C-OH \\ & | \\ & R \end{array}$$

wherein the R's are, independently, hydrogen, or alkyl, e.g., $C_1$-$C_8$ alkyl straight chain or branched or, when taken together, form part of a ring. Examples of suitable allylic alcohols include allyl alcohol, methallyl alcohol, crotyl alcohol, cinnamyl alcohol, 2-butene-1,4-diol and 3-hydroxycyclohexene.

Suitable alkanols are generally $C_1$-$C_{30}$ primary, secondary or tertiary alkanols or diols. They are illustratively represented by the formula $$R^1OH$$

wherein $R^1$ is alkyl or hydroxy alkyl, typically of from 1 to 8 carbon atoms, if the former, or from 2 to 8 carbon atoms if the latter, and in either case the hydrocarbon chain may be straight, branched or cyclic. Illustratively, the alkanol can comprise methanol, n-propanol, isopropanol, ethylene glycol or 1,4-butanediol.

The process of this invention may be carried out at pressures up to 10,000 psig or even higher, but as has been stated, it will preferably be from about 100 psig to 5000 psig, most preferably in the range of from about 300 psig to about 1200 psig. The process may be effected at temperatures ranging from about 10° C. to about 250° C., but, as stated it will be preferably in the range of from about 25° C. to 200° C., and most preferably in the range of from about 100° C. to about 150° C.

The temperature and pressure can be varied within a given reaction so as to improve the efficiency of the hydroformylation of the allylic alcohol and conversion to the 2-alkoxytetrahydrofuran or substituted tetrahydrofuran. For example, a particular process can be conducted under conditions of relatively low temperature and/or pressure so as to enhance the selectivity of the reaction, and can subsequently (without isolation of intermediates) be operated under conditions of higher temperature and/or pressure so as to enhance the conversion of the initial hydroformylation products to the desired alkoxy-substituted products.

The ratio of hydrogen to carbon monoxide employed in the present invention may be varied widely. While mole ratios of hydrogen to carbon monoxide as high as 10 or even higher and as low as 0.1 and even lower may be employed, the preferred ratios are in the range of from about 0.3 to about 2. A more preferable molar ratio of hydrogen to carbon monoxide is in the range of from about 0.8 to about 1.5.

The alkanol may also serve as a solvent as well as co-reactant. However, an inert solvent may also be employed to advantage in the disclosed process. For example, a wide variety of solvents e.g., aromatic and aliphatic hydrocarbons, esters, ethers, nitriles, halogenated hydrocarbons and the like, including benzene, hexane, toluene, mesitylene, xylene, cyclohexane, ethyl acetate, tetrahydrofuran, chlorobenzene, methylene chloride, acetonitrile and the like and mixtures thereof may be employed.

The process may be carried out batchwise or on a continuous or semicontinuous basis. Typically in a continuous or semicontinuous process, the allylic alcohol and alkanol are supplied to a reactor in which the temperature and pressure conditions for reaction are already established. The reactor will also contain the solvent and the catalyst. The products can be isolated by distillation, and the catalyst can be recycled to the reactor in the distillation residue.

Such techniques are well known to those of ordinary skill in the art.

DESCRIPTION OF THE PREFERRED EMBODIMENTS

The following examples are set forth to illustrate the present invention. They are not to be construed to limit the claims in any manner whatsoever.

EXAMPLE 1

2-Methoxy-5,5-dimethyltetrahydrofuran

A 300 cc Autoclave Engineers Magnedrive autoclave is charged with 74.1 grams of 2-methyl-3-buten-2-ol (861 mmol), 75.0 grams of methanol (2.34 mol), 9.6 grams of triphenylphospine (36.6 mmol), and 0.20 grams of hexarhodium hexadecacarbonyl (0.188 mmol, 1.13 meq Rh). The mixture is subjected to 1200 psi of 1:1 $H_2/CO$ and heated to 150° C. In one hour a total of 5300 psi of 1:1 gas is taken up and replenished at 800–1200 psi.

Analysis of the product mixture shows the presence of a very large proportion of a compound subsequently characterized and identified as 2-methoxy-5,5-dimethyltetrahydrofuran. According to quantitative glpc anaylsis (Apiezon column, vs. diphenylmethane internal standard) the yield of this product is 105.5 grams, 94% of the theoretical amount. The structure assignment is confirmed by IR, $^1H$ nmr and mass spectra obtained on the isolated compound. A sample of greater than 99% purity is obtained by distillation (bp 126° C.).

EXAMPLE 2

2-n-Propoxy-5,5-dimethyltetrahydrofuran

The autoclave is charged with 74.1 grams of 2-methyl-3-buten-2-ol (861 mmol), 90.0 grams of n-propanol (1.50 mol), 11.2 grams of triphenylarsine (36.6 mmol), and 0.203 grams of hexarhodium hexadecacarbonyl (0.190 mmol, 1.14 meq Rh). The mixture is subjected to 1:1 $H_2/CO$ as in the above example and heated at 125° C. for 1.5 hours. A total of 6850 psi of 800–1200 psi gas is taken up. Quantitative analysis of the product mixture shows the presence of 121.8 grams of 2-n-propoxy-5,5- dimethyltetrahydrofuran (90% yield), characterized as in the above case, along with a small amount of the 2-hydroxy compound. A sample of the propoxy compound is isolated by distillation (bp 127° C.).

EXAMPLE 3

2-Isopropoxy-5,5-dimethyltetrahydrofuran

The autoclave is charged with 43.1 grams of 2-methyl-3-buten-2-ol (500 mmol), 60.1 grams of isopropanol (1.0 mol), 0.107 grams of hexarhodium hexadecacarbonyl (0.100 mmol, 1.20 meq Rh) and 4.8 grams triphenylphosphine (18.3 mmol). The mixture is heated at 150° C. under replenished 800–1200 psi of 1:1 $H_2/CO$ for one hour, then is cooled and analyzed. The presence of 34.1 grams of 2-isopropoxy-5,5-dimethyltetrahydrofuran (45% yield) along with smaller amounts (5–10% yield) of the 2-hydroxy-5,5-dimethyltetrahydrofuran and bis(5,5-dimethyl-2-tetrahydrofuranyl) ether is indicated.

EXAMPLE 4

Oxo Tetrahydrofuranylation of Ethylene Glcyol

The autoclave is charged with 86.1 grams of 2-methyl-3-buten-2-ol (1.0 mol), 24.8 grams of ethylene glcyol (400 mmol), 0.201 grams of hexarhodium hexadecacarbonyl (0.189 mmol, 1.13 meq Rh), and 11.2 grams of triphenylarsine (36.6 mmol). The mixture is heated for one hour at 125° C. under replenished 800–1200 psi 1:1 $H_2/CO$, then is cooled and analyzed. The products include 34.5 grams of 2-($\beta$-hydroxyethoxy)-5,5-dimethyltetrahydrofuran (54% yield based on ethylene glycol initially charged), 35.0 grams of $\alpha,\beta$-bis (5,5-dimethyl-2-tetrahydrofuranyloxy)ethane (34% yield based on the ethylene glycol), 35.4 grams of 2-hydroxy-5,5-dimethyltetrahydrofuran (30% yield based on the 2-methyl-3-buten-2-ol), and 17.1 grams of bis(5,5-dimethyl-2-tetrahydrofuranyl)ether (16% yield based on the 2-methyl-3-buten-2-ol). Also detected is 3.0 grams of ethylene glycol (12% unconverted).

EXAMPLE 5

2-Methoxy-4-methyltetrahydrofuran

The autoclave is charged with 62.2 grams of methallyl alcohol (861 mmol), 50.0 grams of methanol (1.56 mol), 0.20 grams of hexarhodium hexadecacarbonyl (0.188 mmol, 1.13 meq Rh), and 11.2 grams of triphenylarsine (36.6 mmol), then pressurized to 1200 psi with 1:1 $H_2/CO$ and heated to 125° C. In about one hour from onset of reaction a total of 3300 psi of 1:1 gas is taken up and replenished at 900–1200 psi. The product mixture is cooled and subjected to quantitative glpc analysis (diphenylmethane internal standard, relative response factors determined using product isolated by glpc). The presence of 75.9 grams of 2-methoxy-4-methyltetrahydrofuran is indicated (76% yield). The structure assignment is in accord with the IR, $^1$H nmr and mass spectra of the isolated product.

EXAMPLE 6

2-n-Propoxytetrahydrofuran

The autoclave is charged with 25.0 grams of allyl alcohol (430 mmol), 75.0 grams of n-propanol (1.25 mol), 0.20 grams of hexarhodium hexadecacarbonyl (0.188 mmol, 1.13 meq Rh), and 11.2 grams of triphenylarsine (36.6 mmol), then pressurized with 1200 psi of 1:1 $CO/H_2$ and heated to 125° C. In 45 minutes from onset of reaction a total of 1450 psi of 1:1 gas is taken up and replenished at 900–1200 psi. The product mixture is cooled and subjected to quantitative glpc analysis (n-pentanol internal standard, response factors determined using 2-n-propoxytetrahydrofuran isolated by distillation (bp 145° C.). The presence of 26.6 grams of 2-n-propoxytetrahydrofuran (48% yield) is indicated. The product is identified and characterized as in the examples above.

EXAMPLE 7

2-Isopropoxytetrahydrofuran

The autoclave is charged with 50.0 grams of allyl alcohol (861 mmol), 75.0 grams of isopropyl alcohol (1.25 mol), 0.200 grams of hexarhodium hexadecacarbonyl (0.188 mmol, 1.13 meq Rh), and 9.6 grams of triphenylphosphine (36.6 mmol). The mixture is heated at 125° C. under 800–1200 psi of replenished 1:1 $H_2/CO$, then cooled and analyzed. The presence of 27.6 grams of 2-isopropoxytetrahydrofuran (25% yield, identified and characterized as in the previous examples) is indicated.

EXAMPLE 8

2-Methoxytetrahydrofuran

The autoclave is charged with 50.0 grams of allyl alcohol (861 mmol), 75.0 grams of methanol (2.34 mol), 0.20 grams of hexarhodium hexadecacarbonyl (0.188 mmol, 1.13 meq Rh), and 11.2 grams of triphenylarsine (36.6 mmol). The mixture is heated at 130°–135° C. under replenished 900–1200 psi 1:1 $H_2/CO$ for 45 minutes (3700 psi total uptake), then cooled and analyzed. The presence of 46.6 grams of 2-methoxytetrahydrofuran (53% yield, identified and characterized as in the above examples) is indicated.

EXAMPLE 9

2-Methoxytetrahydrofuran

The autoclave is charged with the reagents described in Example 7, but with 9.6 grams of triphenylphosphine (36.6 mmol) substituted for the triphenylarsine. The mixture is heated under replenished 300–500 psi 1:1 $H_2/CO$ for one hour at 125° C., and one hour at 150° C., then cooled and analyzed. The presence of 39.7 grams of 2-methoxytetrahydrofuran (45% yield) is indicated.

EXAMPLE 10

Unmodified Rhodium Carbonyl Catalyst For 2-Methoxytetrahydrofuran Synthesis

The autoclave is charged with the reagents described in Examples 8 and 9, but without the triphenylarsine or triphenylphosphine modifier. The mixture is heated at 125°–150° C. under 900–1200 psi 1:1 $H_2/CO$ for one hour (1150 psi total gas takeup). Anaylsis of the products shows the presence of about 7 grams of 2-methoxytetrahydrofuran (8% yield). The major product is identified as 1,1-dimethoxypropane.

EXAMPLE 11

Rhodium Dioxide Catalyst Progenitor

The process is carried out as in Example 8, but with 0.152 grams of rhodium dioxide substituted for the hexarhodium hexadecacarbonyl. Analysis of the product mixture in this case shows the presence of 55.9 grams of 2-methoxytetrahydrofuran (64% yield).

To demonstrate the utility of a typical compound prepared by this procedure, 2-methoxytetrahydrofuran is converted to 1,4-butanediol by the following procedure:

A methanolic hydroformylation product mixture obtained as described in Example 8 is distilled through a short path head to provide a co-distillate (boiling range 65°–78° C. of which methanol and 2-methoxytetrahydrofuran (25% by weight according to quantitative glpc analysis) are the major components. The 300 cc Magnedrive autoclave is charged with 50.0 grams of the co-distillate containing 12.3 grams of 2-methoxytetrahydrofuran (120 mmol), 50 ml of water and 5.0 grams of powdered Girdler G-69 nickel catalyst (50% Ni on kieselguhr support, reduced and stabilized). The mixture is subjected to 1000 psi of hydrogen and heated at 125° C. for 30 minutes. The gas uptake corresponds to 350 psi.

The product mixture is filtered and subjected to quantitative glpc analysis, which shows the presence of 10.5 grams of 1,4-butanediol (97% yield) as well as traces of the 2-hydroxytetrahydrofuran intermediate and 2-methoxytetrahydrofuran starting material. Some propanol is also formed by hydrogenation of propionaldehyde present in the starting co-distillate.

It is a matter of common knowledge and experience that butanediol is a commercially useful product finding wide utility in the production of polyesters, particularly, poly(1,4-butylene terephthalate).

Obviously, minor variations will suggest themselves to those skilled in the art in view of the above-identified description. All such obvious modifications are within the full intended scope of the appended claims.

I claim:

1. A process for preparing a 2-alkoxytetrahydrofuran or 2-alkoxy-substituted tetrahydrofuran which comprises contacting an allylic alcohol, carbon monoxide, hydrogen and a corresponding alkanol with a rhodium hydroformylation catalyst.

2. A process as defined in claim 1 carried out at an elevated pressure in the range of 100–5000 psi.

3. A process as defined in claim 2 carried out at a pressure in the range of 300–1200 psi.

4. A process as defined in claim 1 carried out at a temperature between about 25° C. and 200° C.

5. A process as defined in claim 4 carried out at a temperature in the range of 100°–150° C.

6. A process as defined in claim 1 wherein said catalyst comprises rhodium, rhodium carbonyl or rhodium supported on a carrier.

7. A process for preparing a 2-alkoxytetrahydrofuran or 2-alkoxy-substituted tetrahydrofuran which comprises contacting an allylic alcohol, carbon monoxide, hydrogen and a corresponding alkanol with a rhodium catalyst comprising rhodium, rhodium carbonyl or rhodium supported on a carrier, said catalyst also including a ligand selected from an arsine or a phosphine.

8. A process as defined in claim 1 wherein said allylic alcohol comprises allyl alcohol, methallyl alcohol, or 2-methyl-3-buten-2-ol.

9. A process as defined in claim 1 wherein said alkanol comprises methanol, n-propanol, isopropanol or ethylene glycol.

10. A process as defined in claim 1 wherein said allylic alcohol is selected from those of the formula:

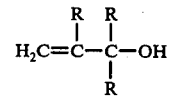

wherein R is hydrogen or alkyl from 1 to 8 carbon atoms and said alkanol is selected from among those of the formula:

wherein $R^1$ is alkyl of from 1 to 8 carbon atoms or hydroxyalkyl of from 2 to 8 carbon atoms.

11. A process for preparing a 2-alkoxytetrahydrofuran or 2-alkoxy-substituted tetrahydrofuran which comprises contacting an allylic alcohol, carbon monoxide, hydrogen and a corresponding alkanol with a rhodium hydroformylation catalyst including a ligand selected from an arsine or a phosphine.